(12) United States Patent
Hashizume et al.

(10) Patent No.: US 10,371,503 B2
(45) Date of Patent: Aug. 6, 2019

(54) SHAPE MEASUREMENT METHOD AND SHAPE MEASUREMENT DEVICE

(71) Applicant: KOBELCO RESEARCH INSTITUTE, INC., Kobe-shi (JP)

(72) Inventors: Hidehisa Hashizume, Kobe (JP); Shunsuke Takami, Kobe (JP); Norihisa Harano, Kobe (JP)

(73) Assignee: KOBELCO RESEARCH INSTITUTE, INC., Kobe-shi (JP)

( * ) Notice: Subject to any disclaimer, the term of this patent is extended or adjusted under 35 U.S.C. 154(b) by 0 days.

(21) Appl. No.: 15/775,073

(22) PCT Filed: Oct. 5, 2016

(86) PCT No.: PCT/JP2016/079594
§ 371 (c)(1),
(2) Date: May 10, 2018

(87) PCT Pub. No.: WO2017/081959
PCT Pub. Date: May 18, 2017

(65) Prior Publication Data
US 2018/0321027 A1 Nov. 8, 2018

(30) Foreign Application Priority Data

Nov. 11, 2015 (JP) ................................. 2015-221281

(51) Int. Cl.
*G01B 11/06* (2006.01)
*G01B 11/24* (2006.01)
(Continued)

(52) U.S. Cl.
CPC .......... *G01B 11/0683* (2013.01); *G01B 11/06* (2013.01); *G01B 11/24* (2013.01); *G01N 21/9503* (2013.01); *G06T 7/60* (2013.01)

(58) Field of Classification Search
CPC ..... G01B 11/06; G01B 11/24; G01B 11/0683; G01B 11/0625; G01B 17/02;
(Continued)

(56) References Cited

U.S. PATENT DOCUMENTS

2013/0228015 A1   9/2013   Wimplinger
2016/0172254 A1   6/2016   Wimplinger

FOREIGN PATENT DOCUMENTS

JP    2003-65724 A    3/2003
JP    2009-156686 A   7/2009
JP    2014-500952 A   1/2014

OTHER PUBLICATIONS

International Search Report dated Dec. 27, 2016 in PCT/JP2016/079594 filed Oct. 5, 2016.

(Continued)

*Primary Examiner* — Tri T Ton
(74) *Attorney, Agent, or Firm* — Oblon, McClelland, Maier & Neustadt, L.L.P.

(57) ABSTRACT

A measurement unit measures a cross-sectional shape of an edge part of a semiconductor wafer. The measurement unit measures a cross-sectional shape of an edge part of a support member. The measurement unit measures a cross-sectional shape of an edge part of a laminated wafer. An analysis unit calculates a thickness of an adhesive agent by subtracting a thickness of the semiconductor wafer and a thickness of the support member from a thickness of the laminated wafer.

7 Claims, 6 Drawing Sheets

(51) Int. Cl.
*G06T 7/60* (2017.01)
*G01N 21/95* (2006.01)

(58) Field of Classification Search
CPC .......... G01B 17/025; G01B 7/06; G06T 7/60;
G01N 21/9503; G01N 21/9501; G01N
21/9505; G01N 2291/0231; G01N
2291/02854; G01N 2291/0289; G01N
2291/044; G01N 2291/2697; G01N
29/043; G01N 29/265; G01N 29/27;
G01N 29/275; H01L 21/67253; H01L
21/67288; H01L 22/12; H01L 22/20
USPC .................................................. 356/625–640
See application file for complete search history.

(56) References Cited

OTHER PUBLICATIONS

International Preliminary Report on Patentability dated May 24, 2018 in PCT/JP2016/079594 (submitting English translation only), 8 pages.

SHAPE MEASUREMENT METHOD AND SHAPE MEASUREMENT DEVICE

TECHNICAL FIELD

The present invention relates to a shape measurement method and a shape measurement device for measuring a cross-sectional shape of an edge part of a laminated wafer that includes: a semiconductor wafer; a support member for reinforcing the semiconductor wafer; and an adhesive agent for laminating the semiconductor wafer and the support member to each other.

BACKGROUND ART

As representative means for measuring a film thickness of a laminated wafer, there has been known a film thickness measurement method which uses FTIR (Fourier Transform Infrared) method (Patent Literature 1). A FTIR measurement device described in Patent Literature 1 includes: an infrared light source 1 capable of emitting infrared rays; a beam splitter 2 which splits a beam of light in two such that a portion of the incident light is allowed to pass through the beam splitter 2 and a remaining portion of the light is reflected; a scanning mirror 3 movable in an optical axis direction; a fixed mirror 4; and a detector 5. The FTIR measurement device detects an interferogram by measuring reflection light by using the detector 5, the reflection light being generated when a wafer is irradiated with an infrared ray, and calculates a film thickness based on the detected interferogram.

An edge part of a laminated wafer is not flat and has a shape with a change in angle. Accordingly, when the above-mentioned FTIR measurement device is applied to the measurement of a thickness of an edge part of a laminated wafer, an interferogram is not detected thus giving rise to a drawback that a thickness of an adhesive agent which forms the laminated wafer cannot be accurately obtained.

Besides the above, as a method for measuring a thickness of an adhesive agent of an edge part of a laminated wafer, a method is used where a laminated wafer is cut and a cross-section of the laminated wafer is observed. However, this method adopts destructive inspection and hence, processing of a wafer requires a considerable time thus giving rise to a drawback that a yield is lowered.

CITATION LIST

Patent Literature

Patent Literature 1: JP 2003-65724 A

SUMMARY OF INVENTION

It is an object of the present invention to provide a technique capable of accurately measuring a thickness of an adhesive agent which forms a laminated wafer.

A shape measurement method according to one aspect of the present invention is a shape measurement method for measuring a cross-sectional shape of an edge part of a laminated wafer that includes: a semiconductor wafer; a support member for reinforcing the semiconductor wafer; and an adhesive agent for laminating the semiconductor wafer and the support member to each other, the method including:

a first measurement step of individually measuring a cross-sectional shape of an edge part of the semiconductor wafer before lamination and a cross-sectional shape of an edge part of the support member before lamination;

a second measurement step of measuring the cross-sectional shape of the edge part of the laminated wafer; and a calculation step of calculating a thickness of the adhesive agent in the laminated wafer by comparing a measurement result of the first measurement step with a measurement result of the second measurement step.

According to the present invention, the thickness of the adhesive agent of the laminated wafer can be accurately measured.

DESCRIPTION OF EMBODIMENTS

Figure 1:
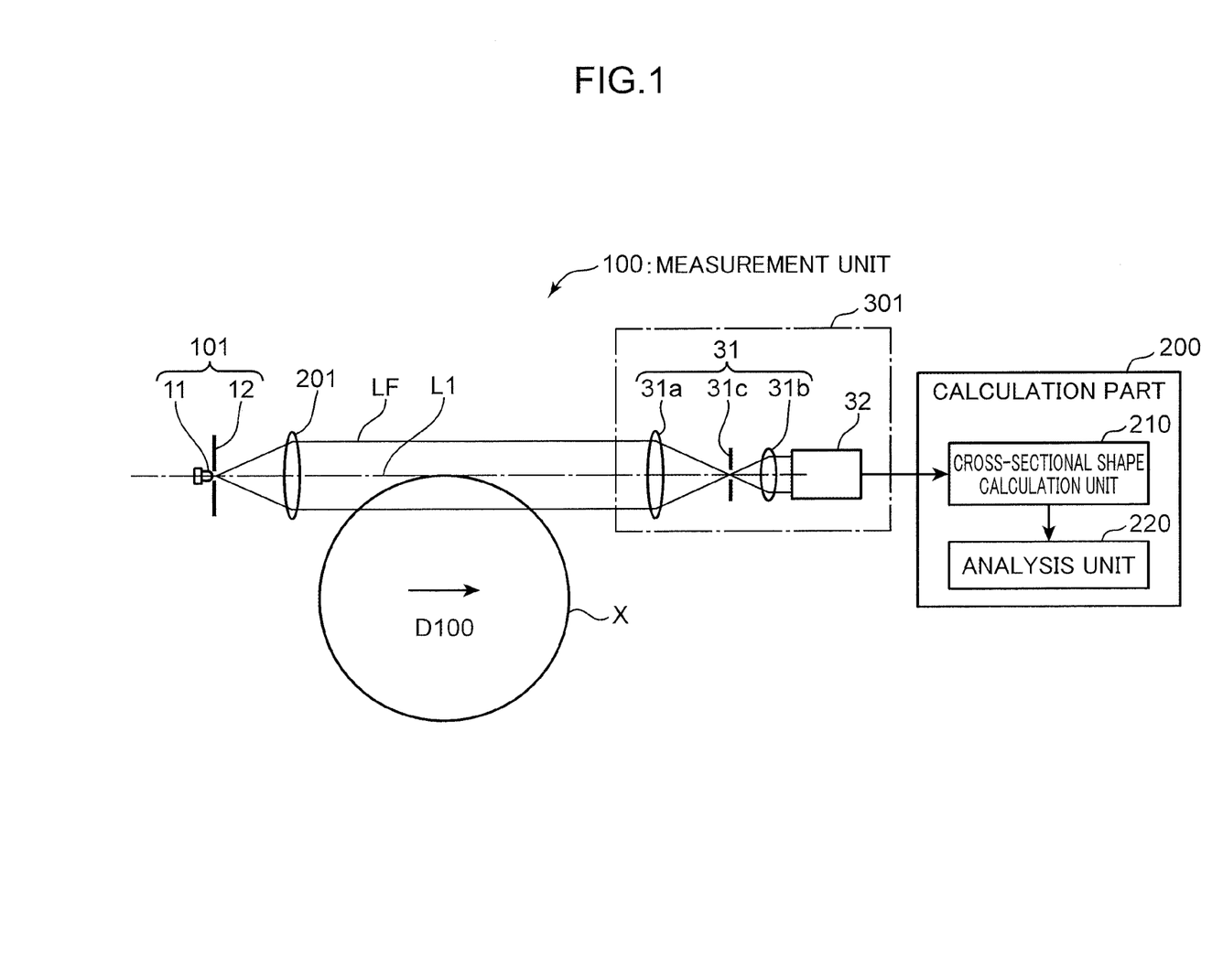
FIG. 1 is a view showing one example of the overall configuration of a shape measurement device according to an embodiment of the present invention.

FIG. 1 is a view showing one example of the overall configuration of a shape measurement device according to an embodiment of the present invention. The shape measurement device according to the embodiment of the present invention is a device for measuring a cross-sectional shape of an edge part of a disk-shaped measurement object X. Hereinafter, the description is made on the assumption that the measurement object X has a disk shape. However, the shape of the measurement object X is an example, and a shape of a main surface of the measurement object X may be other shapes (for example, a quadrangular shape) besides a circular shape.

As the measurement object X, a semiconductor wafer, a support member, and a laminated wafer are adopted. The semiconductor wafer includes any one of silicon, glass, silicon carbide, sapphire, and a compound semiconductor, for example. As such a compound semiconductor, for example, gallium arsenide (GaAs) and gallium nitride (GaN) are used.

The support member is a member for reinforcing a semiconductor wafer, and includes any one of silicon, glass, silicon carbide, sapphire and a compound semiconductor, for example.

The laminated wafer includes the semiconductor wafer, the support member, and an adhesive agent which laminates the semiconductor wafer and the support member to each other.

The shape measurement device according to the embodiment of the present invention includes a measurement unit 100 and a calculation part 200. The measurement unit 100 includes a spot light source 101, a collimator lens 201 which forms a collimating optical system of the spot light source 101, and an imaging optical system 301. The spot light source 101 includes a light source 11 and a pin hole 12. The light source 11 includes a white LED (light emitting diode), for example, and irradiates the measurement object X with a light beam. The pin hole 12 is positioned on a focal position of the collimator lens 201, and is formed of a hole having 4 (diameter) of approximately 100 to 200 μm.

A beam diameter of the light beam emitted from the light source 11 is increased as the light beam passes through the pin hole 12. The light beam increased through the pin hole 12 is formed into a collimated light beam LF (collimated luminous flux) by the collimator lens 201. An optical axis L1 of the collimated light beam LF is parallel to a tangential direction D100 of the measurement object X. The tangential direction D100 is a direction orthogonal to a radial direction of the measurement object X.

In the example shown in FIG. 1, the optical axis L1 is in contact with an outer periphery (edge) of the measurement object X. However, this state is an example, and the optical axis L1 may adopt any direction provided that the direction of the optical axis L1 is the direction that a portion of the collimated light beam LF is shielded by a cross section of the measurement object X.

The imaging optical system 301 includes a telecentric lens 31 and an imaging unit 32. The telecentric lens 31 directs the collimated light beam LF toward the imaging unit 32. The imaging unit 32 includes a two-dimensional CMOS sensor or a CCD sensor, for example, and captures an image (silhouette) of an edge part of the measurement object X, the image being obtained by the light beam which passes through the telecentric lens 31.

The telecentric lens 31 is formed of a telecentric lens having a double telecentric structure, for example, and includes a first lens 31a, a diaphragm 31c, and a second lens 31b. The first and second lenses 31a, 31b are arranged such that a rear-side focal point of the first lens 31a and a front-side focal point of the second lens 31b are aligned with each other. The diaphragm 31c is formed of a variable diaphragm, for example, and is arranged at a focal position of the first and second lenses 31a, 31b. In the telecentric lens 31, a main light beam is parallel to the optical axis L1 in both an object side (measurement object X side) and an image side (imaging unit 32 side). Accordingly, the telecentric lens 31 allows only collimated light beams (including light beams substantially parallel with the optical axis L) to pass therethrough among light beams which pass through the measurement object X.

In the example shown in FIG. 1, a distance between the collimator lens 201 and the first lens 31a is set to approximately 200 mm, for example. The measurement object X is disposed in the collimated light beams LF. In the example shown in FIG. 1, each of the first and the second lenses 31a, 31b is formed of one lens. However, this is only one example. Each of the first and second lenses 31a, 31b may be formed of a lens group including two or more lenses.

The calculation part 200 includes a computer including a central processing unit (CPU), a read-only memory (ROM) and a random-access memory (RAM), for example, and includes a cross-sectional shape calculation unit 210 and an analysis unit 220. The cross-sectional shape calculation unit 210 and the analysis unit 220 are realized by the execution of control programs by the CPU, for example. However, this is an example, and each of the cross-sectional shape calculation unit 210 and the analysis unit 220 may include a dedicated hardware circuit (an application-specific integrated circuit (ASIC) or a field-programmable gate array (FPGA)).

The cross-sectional shape calculation unit 210 calculates parameters indicating a cross-sectional shape of an edge part of a semiconductor wafer based on a measurement result of the semiconductor wafer, the measurement result being measured by the measurement unit 100. In this embodiment, the measurement result of the semiconductor wafer is the image (silhouette) of the edge part of the semiconductor wafer, the image being captured by the imaging unit 32. The cross-sectional shape calculation unit 210 extracts a thickness of the semiconductor wafer from image data which indicates the image of the edge part of the semiconductor wafer, the image being captured by the imaging unit 32, and calculates the extracted thickness as a parameter indicating the cross-sectional shape of the edge part of the semiconductor wafer. Specifically, the cross-sectional shape calculation unit 210 may calculate an actual thickness of the semiconductor wafer by multiplying, by a predetermined coefficient, the thickness of the semiconductor wafer indicated by image data obtained by the capturing of the imaging unit 32. In this embodiment, as the predetermined coefficient, a coefficient for converting a unit length of image data obtained by the capturing of the imaging unit 32 into an actual length may be adopted.

Figure 3:
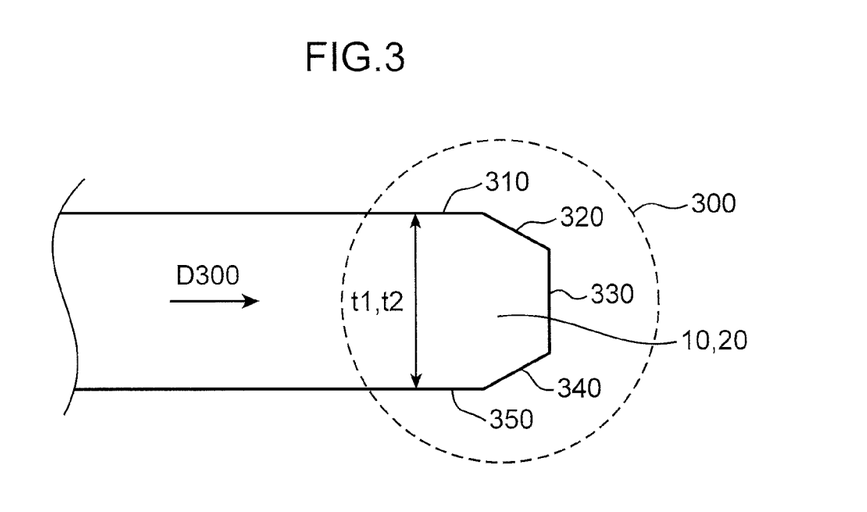
FIG. 3 is a view showing an edge part of a semiconductor wafer and an edge part of a support member in an enlarged manner.

FIG. 3 is a view showing an edge part 300 of a semiconductor wafer 10 and an edge part 300 of a support member 20 in an enlarged manner. Hereinafter, the edge part 300 is described focusing on only the semiconductor wafer 10. The edge part 300 is a region which includes an outer periphery of the semiconductor wafer 10 and an area in the vicinity of the outer periphery. The edge part 300 includes a first flat part 310, a first inclined part 320, a distal end part 330, a second inclined part 340, and a second flat part 350. The first flat part 310 is a plane parallel to the radial direction D300 of the semiconductor wafer 10, and is also a plane continuously formed with one main surface (for example, a front surface) of the semiconductor wafer 10. In this embodiment, the radial direction D300 indicates the direction along a radius of the semiconductor wafer 10 with reference to the center of the semiconductor wafer 10.

The second flat part 350 is a plane parallel to the radial direction D300, and is also a plane continuously formed with the other main surface (for example, a back surface) of the semiconductor wafer 10. The first and second inclined parts 320, 340 are planes inclined at an angle where a thickness of the semiconductor wafer 10 is decreased toward the radial direction D300 as viewed in cross section. The distal end part 330 is a plane which connects the first inclined part 320 and the second inclined part 340 to each other. In the example shown in FIG. 3, the distal end part 330 is orthogonal to the radial direction D300 as viewed in cross section. However, this is an example. For example, the distal end part 330 may have a curved shape which projects outward in the radial direction D300 of the semiconductor wafer 10 as viewed in a cross section or may have a shape inclined with respect to the radial direction D300.

Returning to FIG. 1, the cross-sectional shape calculation unit 210 calculates a distance between the first flat part 310 and the second flat part 350 of the semiconductor wafer 10 as a thickness t1 of the semiconductor wafer 10. The cross-sectional shape calculation unit 210 calculates a thickness t2 of the support member 20 in the same manner as the semiconductor wafer 10. Further, the cross-sectional shape calculation unit 210 calculates a thickness t4 of the laminated wafer 30 in the same manner as the semiconductor wafer 10 (see FIG. 4).

Figure 4:
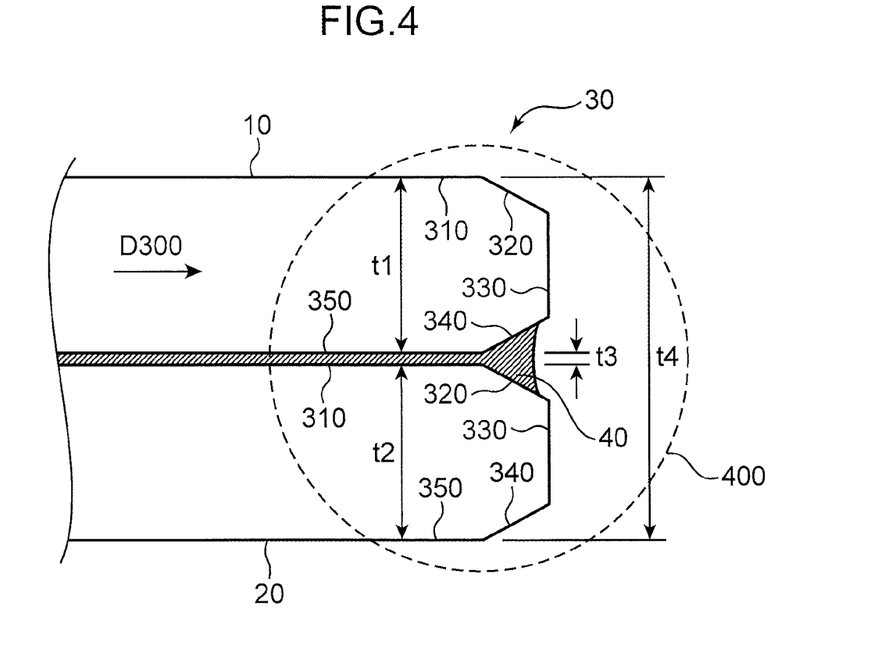
FIG. 4 is a view showing an edge part of a laminated wafer in an enlarged manner.

The analysis unit 220 calculates a thickness of the adhesive agent which forms the laminated wafer, by performing a comparison among a measurement result of a cross-sectional shape of the edge part 300 of the semiconductor wafer 10 before lamination, a measurement result of a cross-sectional shape of the edge part 300 of the support member 20 before lamination; and a measurement result of a cross-sectional shape of an edge part 400 of the laminated wafer 30.

FIG. 4 is a view showing the edge part 400 of the laminated wafer 30 in an enlarged manner. The edge part 400 is a region which includes an outer periphery of the laminated wafer 30 and an area in the vicinity of the outer periphery. The laminated wafer 30 is formed by sequentially stacking the semiconductor wafer 10, an adhesive agent 40, and the support member 20. The adhesive agent 40 is made of a material which makes the semiconductor wafer 10 and the support member 20 adhere to each other.

The cross-sectional shape of the edge part 400 is formed of: the first flat part 310, the first inclined part 320, and the distal end part 330 of the semiconductor wafer 10; the distal end part 330, the second inclined part 340, and the second flat part 350 of the support member 20; and an outer periphery of the adhesive agent 40. The adhesive agent 40 exists in a sector-shaped region formed between the second inclined part 340 of the semiconductor wafer 10 and the first inclined part 320 of the support member 20. Accordingly, the outer periphery of the adhesive agent 40 is formed by the adhesive agent 40 within this sector-shaped region. Further, the adhesive agent 40 is interposed between the second flat part 350 of the semiconductor wafer 10 and the first flat part 310 of the support member 20 such that the second flat part 350 of the semiconductor wafer 10 and the first flat part 310 of the support member 20 become parallel to each other.

The analysis unit 220 calculates a thickness t3 of the adhesive agent 40 by subtracting the thickness t1 of the semiconductor wafer 10 and the thickness t2 of the support member 20 which are calculated by the cross-sectional shape calculation unit 210 from the thickness t4 of the laminated wafer 30 calculated by the cross-sectional shape calculation unit 210.

In this embodiment, the thickness t4 of the laminated wafer 30 indicates, in the laminated wafer 30, a distance from the first flat part 310 of the semiconductor wafer 10 to the second flat part 350 of the support member 20. The thickness t3 of the adhesive agent 40 indicates, in the laminated wafer 30, a distance from the second flat part 350 of the semiconductor wafer 10 to the first flat part 310 of the support member 20.

Figure 2:
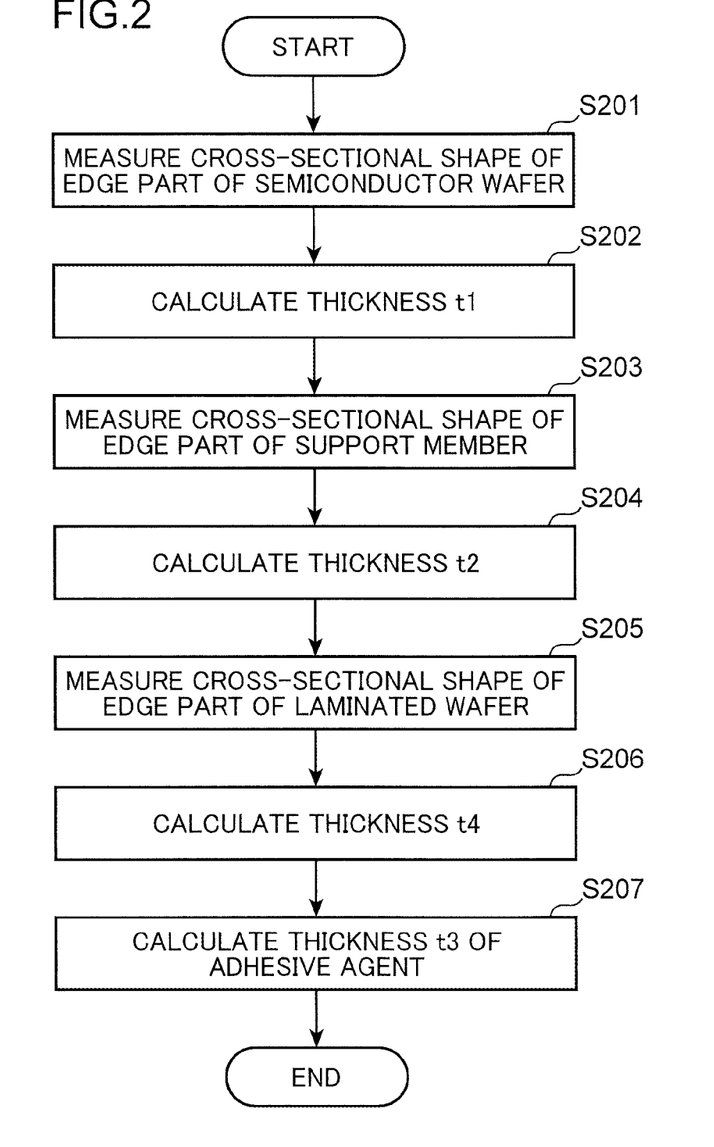
FIG. 2 is a flowchart showing one example of processing performed by the shape measurement device according to the embodiment of the present invention.

Next, processing performed by the shape measurement device according to the embodiment of the present invention is described. FIG. 2 is a flowchart showing one example of processing performed by the shape measurement device according to the embodiment of the present invention. Firstly, the measurement unit 100 measures the cross-sectional shape of the edge part 300 of the semiconductor wafer 10 (S201).

In this step, the imaging unit 32 captures an image of the edge part 300 of the semiconductor wafer 10, the image being formed by emitting the light beam toward the tangential direction of the outer periphery of the semiconductor wafer 10 by the light source 11. With such capturing, the cross-sectional shape of the edge part 300 of the semiconductor wafer 10 is measured.

Next, the cross-sectional shape calculation unit 210 calculates the thickness t1 of the semiconductor wafer 10 based on a measurement result obtained in S201 (S202).

Then, the measurement unit 100 measures the cross-section shape of the edge part 300 of the support member 20 (S203). In this step, in the same manner as the semiconductor wafer 10, the cross-sectional shape of the edge part 300 of the support member 20 is measured by capturing an image of the support member 20 by the imaging unit 32.

Next, the cross-sectional shape calculation unit 210 calculates the thickness t2 of the support member 20 based on a measurement result obtained in S203 (S204).

Next, the measurement unit 100 measures the cross-sectional shape of the edge part 400 of the laminated wafer 30 (S205). In this step, in the same manner as the semiconductor wafer 10, the cross-sectional shape of the edge part 400 of the laminated wafer 30 is measured by capturing an image of the laminated wafer 30 by the imaging unit 32. In this step, the laminated wafer 30 which forms a measurement object is the laminated wafer 30 formed by making the semiconductor wafer 10 measured in S201 and the support member 20 measured in S202 adhere to each other by the adhesive agent 40.

Then, the cross-sectional shape calculation unit 210 calculates the thickness t4 of the laminated wafer 30 based on a measurement result obtained in S205 (S206).

Next, the analysis unit 220 calculates the thickness t3 of the adhesive agent 40 by subtracting the thickness t1 of the semiconductor wafer 10 and the thickness t2 of the support member 20 from the thickness t4 of the laminated wafer 30 (S207). That is, the analysis unit 220 calculates the thickness t3 by performing a calculation of $t3=t4-(t1+t2)$.

As described above, according to the shape measurement device of the embodiment of the present invention, based on the measurement result of the cross-sectional shape of the edge part of the semiconductor wafer 10 before lamination, the measurement result of the cross-sectional shape of the edge part of the support member 20 before lamination, and the measurement result of the cross-sectional shape of the edge part of the laminated wafer 30, the thickness t1 of the semiconductor wafer 10, the thickness t2 of the support member 20, and the thickness t4 of the laminated wafer 30 can be respectively detected. Then, the thickness t3 of the adhesive agent 40 can be calculated using the calculated thicknesses t1, t2, t4. Accordingly, the thickness t3 of the adhesive agent 40 which forms the laminated wafer 30 can be accurately calculated. As a result, an analysis of a cross-sectional shape of the edge part 400 of the laminated wafer 30 can be accurately performed.

The following modifications can be adopted with respect to the embodiment of the present invention.

(1) In FIG. 1, the measurement unit 100 measures the measurement object X by a shadow imaging method. However, the present invention is not limited to such a method, and the measurement object X may be measured by any one of a line scanning imaging method and a microscope imaging method.

Figure 5:
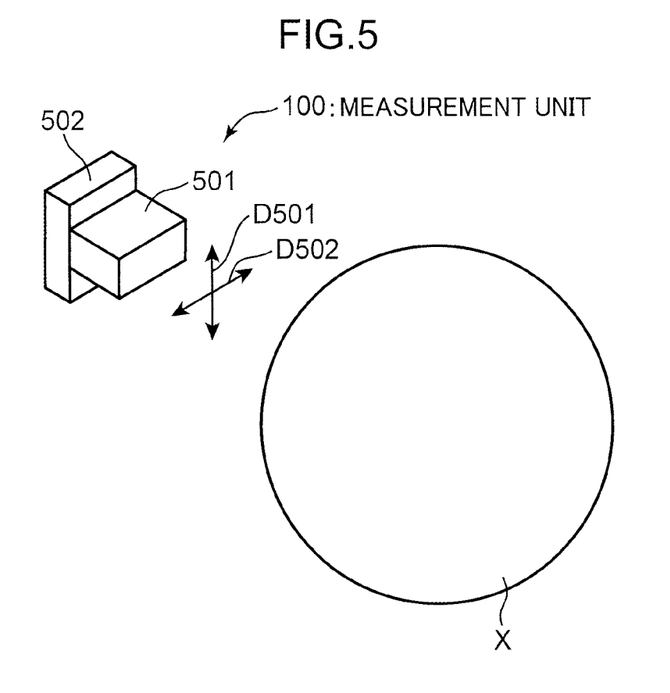
FIG. 5 is a view showing one example of the configuration of a measurement unit for measuring a cross-sectional shape of an edge part of a measurement object X by a line scanning measurement method.

FIG. 5 is a view showing one example of the configuration of the measurement unit 100 which measures a cross-sectional shape of an edge part of a measurement object X by a line scanning measurement method. In FIG. 5, the measurement unit 100 includes a line sensor 501 and a scanning mechanism 502. The line sensor 501 is, for example, formed of a one-dimensional CMOS sensor or CCD sensor where a plurality of light receiving elements are arranged in a main scanning direction D502, and the line sensor 501 measures a cross-sectional shape of an edge part of a measurement object X in accordance with one line unit. In such a measurement unit 100, the line sensor 501 is arranged such that the main scanning direction D502 orthogonally intersects with a main surface of the measurement object X. The scanning mechanism 502 is formed of an actuator, for example, and moves the line sensor 501 in a sub scanning direction D501 orthogonal to the main scanning direction D502. Accordingly, the line sensor 501 repeatedly captures an image of the measurement object X in accordance with one line unit while being moved in the sub scanning direction D501 by the scanning mechanism 502 thus measuring the cross-sectional shape of the edge part of the measurement object X. In the example shown in FIG. 5, the line sensor 501 is moved in the sub scanning direction D501, but the present invention is not limited thereto. That is, the line sensor 501 may be fixed, and the measurement object X may be moved in the sub scanning direction D501.

Figure 6:
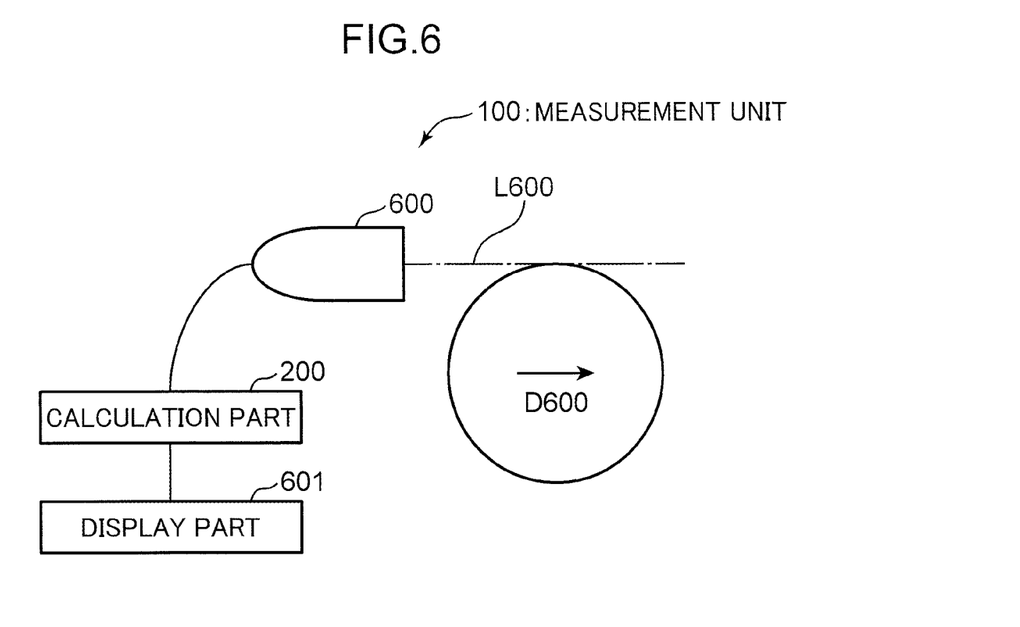
FIG. 6 is a view showing one example of the configuration of a measurement unit for measuring a cross-sectional shape of an edge part of a measurement object X by a microscope imaging method.

FIG. 6 is a view showing one example of the configuration of the measurement unit 100 for measuring a cross-sectional shape of an edge part of a measurement object X by a microscope imaging method. In FIG. 6, the measurement unit 100 is formed of a microscope 600. The microscope 600 is an enlarging display device which includes a color camera, an illumination, a lens and a connection cable. In FIG. 6, the microscope 600 is arranged such that an optical axis L600 is directed to a tangential direction D600 of the measurement object X.

The microscope 600 captures an image of the edge part of the measurement object X, and outputs captured data to the calculation part 200. The calculation part 200 displays the captured data on a display part 601. Accordingly, the display part 601 displays an enlarged image of the edge part of the measurement object X.

A user may measure a thickness of the measurement object X by visually observing an enlarged view of the measurement object X which is displayed on the display part 601 in an enlarged manner. Alternatively, the calculation part 200 may measure a thickness of the measurement object X by performing image processing on the captured data outputted from the microscope 600.

(2) In the flowchart shown in FIG. 2, the cross-sectional shape of the edge part 300 of the semiconductor wafer 10 is measured, and the cross-sectional shape of the edge part 300 of the support member 20 is measured in this order. However, this order may be reversed. That is, such measurement may be performed such that the cross-sectional shape of the edge part 300 of the support member 20 is measured, and the cross-sectional shape of the edge part 300 of the semiconductor wafer 10 is measured in this order.

A shape measurement method according to one aspect of the present invention is a shape measurement method for measuring a cross-sectional shape of an edge part of a laminated wafer which includes: a semiconductor wafer; a support member for reinforcing the semiconductor wafer; and an adhesive agent for laminating the semiconductor wafer and the support member to each other, the method including:

a first measurement step of individually measuring a cross-sectional shape of an edge part of the semiconductor wafer before lamination and a cross-sectional shape of an edge part of the support member before lamination;

a second measurement step of measuring the cross-sectional shape of the edge part of the laminated wafer; and a calculation step of calculating a thickness of the adhesive agent in the laminated wafer by comparing a measurement result of the first measurement step with a measurement result of the second measurement step.

With such a configuration, the first measurement step of individually measuring the cross-sectional shape of the edge part of the semiconductor wafer before lamination and the cross-sectional shape of the edge part of the support member before lamination, and the second measurement step of measuring the cross-sectional shape of the edge part of the laminated wafer are performed. Then, the thickness of the adhesive agent which forms the laminated wafer is detected by comparing the measurement result of the first measurement step with the measurement result of the second measurement step to each other. Accordingly, the thickness of the adhesive agent which forms the laminated wafer can be accurately detected.

In the above-mentioned embodiment, the semiconductor wafer may include any one of silicon, glass, silicon carbide, sapphire, and a compound semiconductor.

With such a configuration, by forming the semiconductor wafer using any one of silicon, glass, silicon carbide, sapphire, and a compound semiconductor, a thickness of an adhesive agent can be accurately detected.

In the above-mentioned configuration, the support member may be made of any one of silicon, glass, silicon carbide, sapphire, and a compound semiconductor.

With such a configuration, by forming the support member using any one of silicon, glass, silicon carbide, sapphire, and a compound semiconductor, a thickness of an adhesive agent can be accurately detected.

In the above-mentioned embodiment, in the first and second measurement steps, the cross-sectional shape of each of the edge parts may be measured using any one of a shadow imaging method, a line scanning imaging method, and a microscope imaging method.

With such a configuration, in the first and second measurement steps, the cross-sectional shape of each of the edge parts can be measured using any one of a shadow imaging method, a line scanning imaging method, and a microscope imaging method and hence, a thickness of an adhesive agent can be accurately detected.

In the above-mentioned embodiment, in the first measurement step, the measurement may be performed by using a thickness of the semiconductor wafer and a thickness of the support member as parameters indicating the cross-sectional shapes of the edge parts, in the second measurement step, the measurement may be performed by using a thickness of the laminated wafer as a parameter indicating the cross-sectional shape of the edge part, and in the calculation step, the thickness of the adhesive agent may be calculated by subtracting the thickness of the semiconductor wafer and the thickness of the support member which are measured in the first measurement step from the thickness of the laminated wafer measured in the second measurement step.

With such a configuration, the thickness of the adhesive agent can be calculated by subtracting the thickness of the semiconductor wafer and the thickness of the support member which are measured in the first measurement step from the thickness of the laminated wafer measured in the second measurement step. Accordingly, the thickness of the adhesive agent can be accurately detected.

In the above-mentioned embodiment, the edge part of the semiconductor wafer may include the first flat part continuously formed with one main surface of the semiconductor wafer and the second flat part continuously formed with another main surface of the semiconductor wafer, the edge part of the support member may include the first flat part continuously formed with one main surface of the support member and the second flat part continuously formed with another main surface of the support member, the adhesive agent may be interposed at least between the second flat part of the semiconductor wafer and the first flat part of the support member, the thickness of the semiconductor wafer may be a distance between the first flat part of the semiconductor wafer and the second flat part of the semiconductor wafer, the thickness of the support member may be a distance between the first flat part of the support member and the second flat part of the support member, the thickness of the laminated wafer may be a distance between the first flat part of the semiconductor wafer and the second flat part of the support member, and the thickness of the adhesive agent may be, in the laminated wafer, a distance from the second flat part of the semiconductor wafer to the first flat part of the support member.

The invention claimed is:

1. A shape measurement method for measuring a cross-sectional shape of an edge part of a laminated wafer that includes: a semiconductor wafer; a support member for reinforcing the semiconductor wafer; and an adhesive agent for laminating the semiconductor wafer and the support member to each other, the method comprising:
   a first measurement step of individually measuring a cross-sectional shape of an edge part of the semiconductor wafer before lamination and a cross-sectional shape of an edge part of the support member before lamination;
   a second measurement step of measuring the cross-sectional shape of the edge part of the laminated wafer; and
   a calculation step of calculating a thickness of the adhesive agent in the laminated wafer by comparing a measurement result of the first measurement step with a measurement result of the second measurement step.

2. The shape measurement method according to claim 1, wherein the semiconductor wafer includes silicon, glass, silicon carbide, sapphire or a compound semiconductor.

3. The shape measurement method according to claim 1, wherein the support member includes silicon, glass, silicon carbide, sapphire or a compound semiconductor.

4. The shape measurement method according to claim 1, wherein in the first and second measurement steps, the cross-sectional shape of each of the edge parts is measured using any one of a shadow imaging method, a line scanning imaging method, and a microscope imaging method.

5. The shape measurement method according to claim 1, wherein in the first measurement step, the measurement is performed by using a thickness of the semiconductor wafer and a thickness of the support member as parameters indicating the cross-sectional shapes of the edge parts of the semiconductor wafer and the support member,
   in the second measurement step, the measurement is performed by using a thickness of the laminated wafer as a parameter indicating the cross-sectional shape of the edge part of the laminated wafer,
   in the calculation step, the thickness of the adhesive agent is calculated by subtracting the thickness of the semiconductor wafer and the thickness of the support member which are measured in the first measurement step from the thickness of the laminated wafer measured in the second measurement step.

6. The shape measurement method according to claim 5, wherein
   the edge part of the semiconductor wafer includes a first flat part continuously formed with one main surface of the semiconductor wafer, and a second flat part continuously formed with another main surface of the semiconductor wafer,
   the edge part of the support member includes a first flat part continuously formed with one main surface of the support member and a second flat part continuously formed with another main surface of the support member,
   the adhesive agent is interposed at least between the second flat part of the semiconductor wafer and the first flat part of the support member,
   the thickness of the semiconductor wafer is a distance between the first flat part of the semiconductor wafer and the second flat part of the semiconductor wafer,
   the thickness of the support member is a distance between the first flat part of the support member and the second flat part of the support member,
   the thickness of the laminated wafer is a distance between the first flat part of the semiconductor wafer and the second flat part of the support member in the laminated wafer, and
   the thickness of the adhesive agent is, in the laminated wafer, a distance between the second flat part of the semiconductor wafer and the first flat part of the support member.

7. A shape measurement device for measuring a cross-sectional shape of an edge part of a laminated wafer including: a semiconductor wafer; a support member for reinforcing the semiconductor wafer; and an adhesive agent for laminating the semiconductor wafer and the support member to each other, the shape measurement device comprising:
   a measurement unit that individually measures a cross-sectional shape of an edge part of the semiconductor wafer before lamination, a cross-sectional shape of an edge part of the support member before lamination, and the cross-sectional shape of the edge part of the laminated wafer; and
   a calculation unit that calculates a thickness of the adhesive agent which forms the laminated wafer, by performing a comparison among a measurement result of the cross-sectional shape of the edge part of the semiconductor wafer before lamination, a measurement result of the cross-sectional shape of the edge part of the support member before lamination, and a measurement result of the cross-sectional shape of the edge part of the laminated wafer.

* * * * *